(12) United States Patent
Aggerholm et al.

(10) Patent No.: US 8,685,054 B2
(45) Date of Patent: Apr. 1, 2014

(54) VALVULOPLASTY BALLOON CATHETER

(75) Inventors: Steen Aggerholm, St. Heddinge (DK); Tue Thuren Bödewadt, Herfoelge (DK); Per Elgaard, Haslev (DK); Christina Rauf Hansen, Koebenhavn (DK); Anders Scheel Klausen, Naestved (DK); Thomas Lysgaard, Solroed Strand (DK); Allan Torp, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 43 days.

(21) Appl. No.: 13/283,136

(22) Filed: Oct. 27, 2011

(65) Prior Publication Data

US 2012/0277785 A1  Nov. 1, 2012

(30) Foreign Application Priority Data

Oct. 27, 2010 (GB) .................................. 1018151.9

(51) Int. Cl.
*A61M 29/00* (2006.01)
(52) U.S. Cl.
USPC .... 606/194; 606/192; 604/96.01; 604/103.08
(58) Field of Classification Search
USPC ................ 606/192–199, 159; 604/96.01, 604/103.01–103.08, 104–106; 623/1.11
See application file for complete search history.

(56) References Cited

U.S. PATENT DOCUMENTS

| 5,226,887 | A | * | 7/1993 | Farr et al. ................. 604/103.09 |
| 5,395,331 | A | | 3/1995 | O'Neill et al. |
| 5,423,745 | A | | 6/1995 | Todd et al. |
| 5,720,726 | A | | 2/1998 | Marcadis et al. |
| 5,792,106 | A | * | 8/1998 | Mische .................... 604/103.01 |
| 5,807,326 | A | | 9/1998 | O'Neill et al. |
| 6,013,055 | A | * | 1/2000 | Bampos et al. .......... 604/103.07 |
| 6,027,510 | A | * | 2/2000 | Alt ................................ 606/108 |
| 6,129,706 | A | | 10/2000 | Janacek |
| 7,008,438 | B2 | | 3/2006 | O'Brien |
| 7,083,639 | B2 | * | 8/2006 | Guinan et al. .................. 623/1.1 |
| 7,306,616 | B2 | * | 12/2007 | Eidenschink et al. ........ 606/194 |

(Continued)

FOREIGN PATENT DOCUMENTS

| EP | 0204218 A1 | 12/1986 |
| WO | 9508965 A1 | 4/1995 |

(Continued)

OTHER PUBLICATIONS

PCT/US2011/058084, International Search Report, Cook Medical Technologies LLC, Oct. 27, 2011.

(Continued)

*Primary Examiner* — Katherine M Dowe
*Assistant Examiner* — Katrina Stransky
(74) *Attorney, Agent, or Firm* — Richard J. Godlewski

(57) ABSTRACT

A valvuloplasty balloon assembly includes a balloon (50) provided with end shoulders (64, 66) preferably integral with end cones (54, 56) of the balloon (50). The end shoulders (64, 66) provide a substantially perpendicular stop shoulder (68) at either end of the cylindrical portion (52) of the balloon (50). The restraining shoulders (64, 66) act to hold the balloon (50) within a valve (16) of a heart (10), for instance. This prevents unwanted slippage of the balloon (50) during a valvuloplasty procedure and thus prevents possible damage caused as a result of such slippage.

20 Claims, 5 Drawing Sheets

(56) References Cited

U.S. PATENT DOCUMENTS

| | | | |
|---|---|---|---|
| 7,566,319 | B2 | 7/2009 | McAuley et al. |
| 7,819,841 | B2 * | 10/2010 | Horrigan ........................ 604/104 |
| 2005/0075662 | A1 | 4/2005 | Pedersen et al. |
| 2006/0167407 | A1 | 7/2006 | Weber et al. |
| 2006/0182873 | A1 * | 8/2006 | Klisch et al. .................... 427/2.1 |
| 2007/0112300 | A1 * | 5/2007 | Roman et al. ............ 604/103.07 |
| 2009/0005732 | A1 | 1/2009 | Rice et al. |
| 2009/0254113 | A1 * | 10/2009 | Nolan et al. .................. 606/194 |
| 2011/0218564 | A1 * | 9/2011 | Drasler et al. ................ 606/192 |

FOREIGN PATENT DOCUMENTS

| | | |
|---|---|---|
| WO | 9618427 A1 | 6/1996 |
| WO | 03039628 A3 | 5/2003 |
| WO | 2006089115 A1 | 8/2006 |

OTHER PUBLICATIONS

PCT/US2011/058084, International Written Opinion, Cook Medical Technologies LLC, Oct. 27, 2011.

* cited by examiner

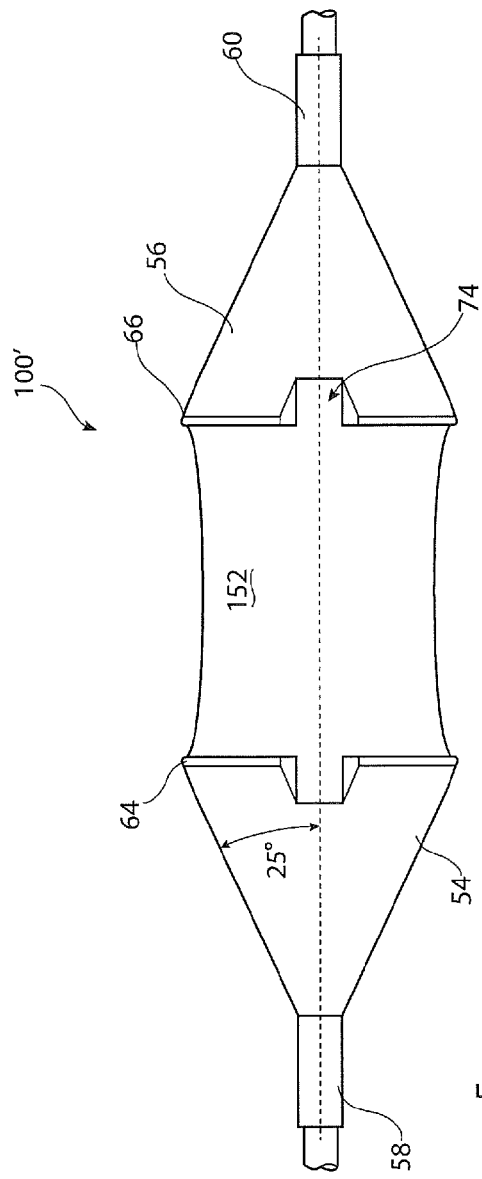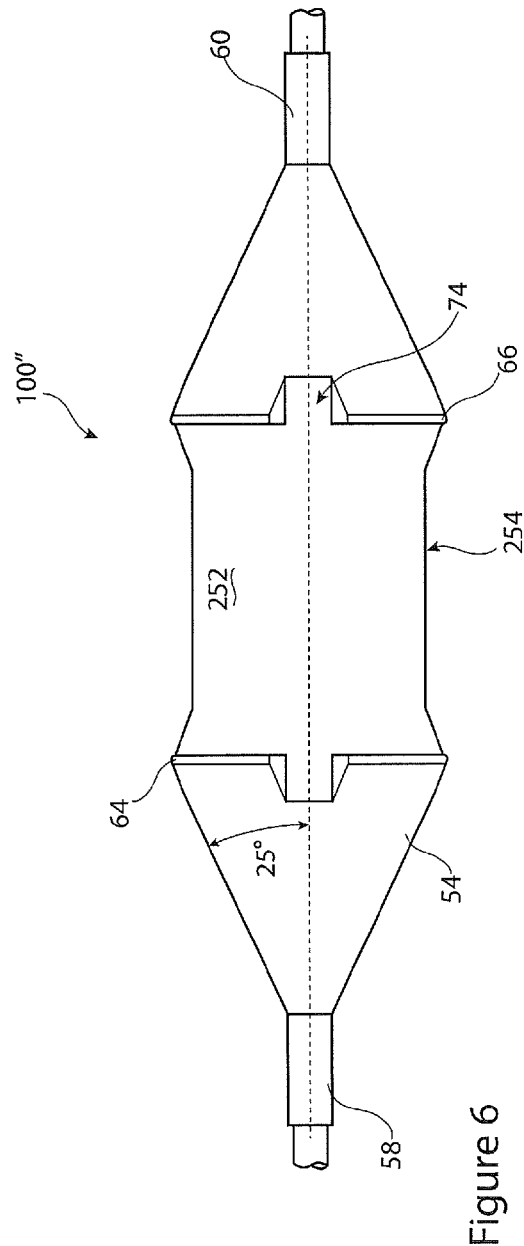

VALVULOPLASTY BALLOON CATHETER

TECHNICAL FIELD

The present invention relates to a balloon assembly particularly for valvuloplasty applications.

BACKGROUND ART

Valvular stenosis is a defect which may be congenital, developing in the foetus and present at birth, or may develop over time, for instance as an effect of some other disorder. For example, mitral valve stenosis in adults is rarely congenital and can occur as a result of rheumatic fever or calcium obstruction in the valve.

Congenital valvular stenosis is found in around one in every 1,000 newborns. In some instances health problems affecting the mother during pregnancy is thought to contribute to the defect. About 5% of all cardiac defects are found to relate to valvular stenosis. Valvular abnormalities are found in children of both sexes, but the vast majority of adult valvular stenosis is found to occur in men. Most adults with Mitral stenosis are women who have suffered rheumatic fever as children.

Reduced valvular function is also experienced in some patients, caused by the valves failing to open fully.

A variety of treatments have been attempted to treat these conditions, including diuretic therapy, anticoagulant therapy and open surgery. More recently, however, balloon valvuloplasty has been performed, both on children and on adults. The procedure is to force the valve open, with the aim that so doing will cure the stenosis and prompt normal valve function. In balloon valvuloplasty, a small balloon tipped catheter is positioned within the valve opening and the balloon then inflated to prise the valve leaflets apart. The balloon has to have an inflated diameter no greater than the diameter of the valve seat in order not to damage the valve. The balloon is then deflated and removed.

In order not to cause trauma or damage to the heart, balloon valvuloplasty must be performed quickly.

Often, balloon valvuloplasty can sure the valve function and thus avoid the need for open heart surgery and valve replacement. It is therefore seen as an important method of treatment.

There is a risk, however, during balloon valvuloplasty that the balloon catheter jumps or slips out of position either out of the heart or into the heart, as a result of heart/valve function as well as of the dynamics of the inflating balloon. Such slippage can either lead to an abortive procedure or to damage of the heart.

Balloon catheter assemblies for a variety of treatments have been disclosed in WO-03/039,628, U.S. Pat. No. 6,129, 706, U.S. Pat. No. 7,008,438, EP-0,204,218, US-2005/0,075, 662, US-2006/0,167,407, US-2009/0,005,732, U.S. Pat. No. 5,395,331, U.S. Pat. No. 5,720,726, U.S. Pat. No. 5,423,745 and U.S. Pat. No. 7,566,319.

DISCLOSURE OF THE INVENTION

The present invention seeks to provide an improved balloon catheter for valvuloplasty procedures.

According to an aspect of the present invention, there is provided a balloon catheter assembly including an inflatable balloon provided with a body portion having first and second ends and a longitudinal axis extending from the first end to the second end; the balloon being formed of balloon material; and at least one circumferentially extending rib element at or proximate one of said first and second ends, the rib element being formed of balloon material and being inflatable with the balloon; the rib element, when inflated, including a retaining shoulder facing the body portion of the balloon and a wall portion facing a direction opposite the body portion; wherein said retaining shoulder has an interior angle to the longitudinal axis which is greater than the interior angle of the wall portion to the longitudinal axis of the balloon; the rib element being discontinuous around the circumference of the balloon and being formed of a plurality of circumferentially aligned rib portions spaced from one another by a tether element.

The rib, which could be said to have a wedge shape when viewed in side elevation, acts to retain the balloon in position during inflation and use. The fact that the rib is inflatable allows the balloon to be wrapped to a small footprint and also allows the rib to be made larger and/or higher above the surface of the body portion when inflated than is possible with, for instance, solid ribs.

The discontinuities in the rib or ribs, providing tether elements between the rib portions, ensure that these do not flatten during inflation of the balloon. In the preferred embodiment, the or each rib is formed of at least three sections preferably of similar sizes to one another.

It has been found that such discontinuities also assist in the deflation of the balloon, in that they cause the balloon to collapse into the tethers or discontinuities, leaving wings where the rib portions are located. Specifically, the discontinuities or tethers will, on application of a vacuum to the balloon, be pulled inwardly towards the centre of the balloon and the ribs will generally fold along the length of the balloon. The balloon can then be readily wrapped, often without the need for a specialised wrapping tool.

Advantageously, the retaining shoulder has an interior angle to the surface of the body member which is at least 70 degrees, advantageously at least 80 degrees and in the preferred embodiment substantially 90 degrees.

The retaining shoulder may comprise all of or part of the portion of the or each rib facing the body portion of the balloon.

In the preferred embodiment, there are provided first and second ribs, located at or proximate the first and second ends of the body portion of the balloon, each of said first and second ribs having a retaining shoulder facing the opposing end of the balloon and a wall portion at or facing the end of the balloon at which the rib is located. The provision of two ribs of this nature can act to "lock" the balloon in position, for instance across a heart valve. Once inflated, the ribs ensure that the balloon is not able to slip out of position, in either direction of motion.

The or each rib preferably has an inflated height, measured from the surface of the body portion, of at least 0.5 millimeters, preferably between 0.5 millimeters and 4.0 millimeters. For a cardiac application, the rib or ribs may have an inflated height of 2.0 to 4.0 millimeters.

The rib or ribs are preferably formed of the same material as the body portion of the balloon and in the preferred embodiment are a continuation of the balloon wall, that is have a wall thickness which is the same or substantially the same as that of the balloon. This gives the ribs a compliancy which is consistent with that of the majority of the balloon and also allows the ribs to be formed in the same process as the remainder of the balloon, typically from raw tubing which is inflated in a mold to the final desired shape of the balloon. In this example, the mold would have impressions representative of the shapes, sizes and positions of the ribs.

In a practical embodiment, the balloon includes at least one intermediate rib extending circumferentially around the body portion, and in the preferred embodiment between the first and second end ribs. It is preferred, however, that there are provided two such intermediate ribs, spaced from one another and advantageously evenly along the body portion of the balloon.

Two, or an even number of intermediate ribs, can enable their positioning such that the centre point of the balloon is free of such ribbing. This can assist in locating the balloon at its centre point across, instance, a valve.

It is preferred, but not essential, that the or each intermediate rib has a height which is less than the height of the end rib or ribs.

The preferred embodiments are used in carrying out valvuloplasty treatment of the heart valves. The body portion preferably has an inflated diameter of around 18 to 25 millimeters.

The balloon is preferably made from a substantially non-compliant material such as Pebax, nylon 12, polyethylene, PET and polyurethane.

The balloon may be made of a single layer or of a plurality of layers useful, for instance, in optimising balloon strength, wrappability and the like.

The balloon is typically fitted to a catheter element, the latter provided with at least one lumen for inflating the balloon. The catheter element may also include other lumens, for instance for a guide wire, for the administration of contrast media and so on.

BRIEF DESCRIPTION OF THE DRAWINGS

Embodiment of the present invention are described below, by way of example only, with reference to the accompanying drawings, in which:

FIG. 2b is an end view of the balloon of FIG. 2a;

FIG. 3b is an end view of the balloon of FIG. 3a;

FIG. 5 is a side elevational view of another embodiment of valvuloplasty balloon; and FIG. 6 is a side elevational view of another embodiment of valvuloplasty balloon.

DESCRIPTION OF THE PREFERRED EMBODIMENTS

Figure 1:
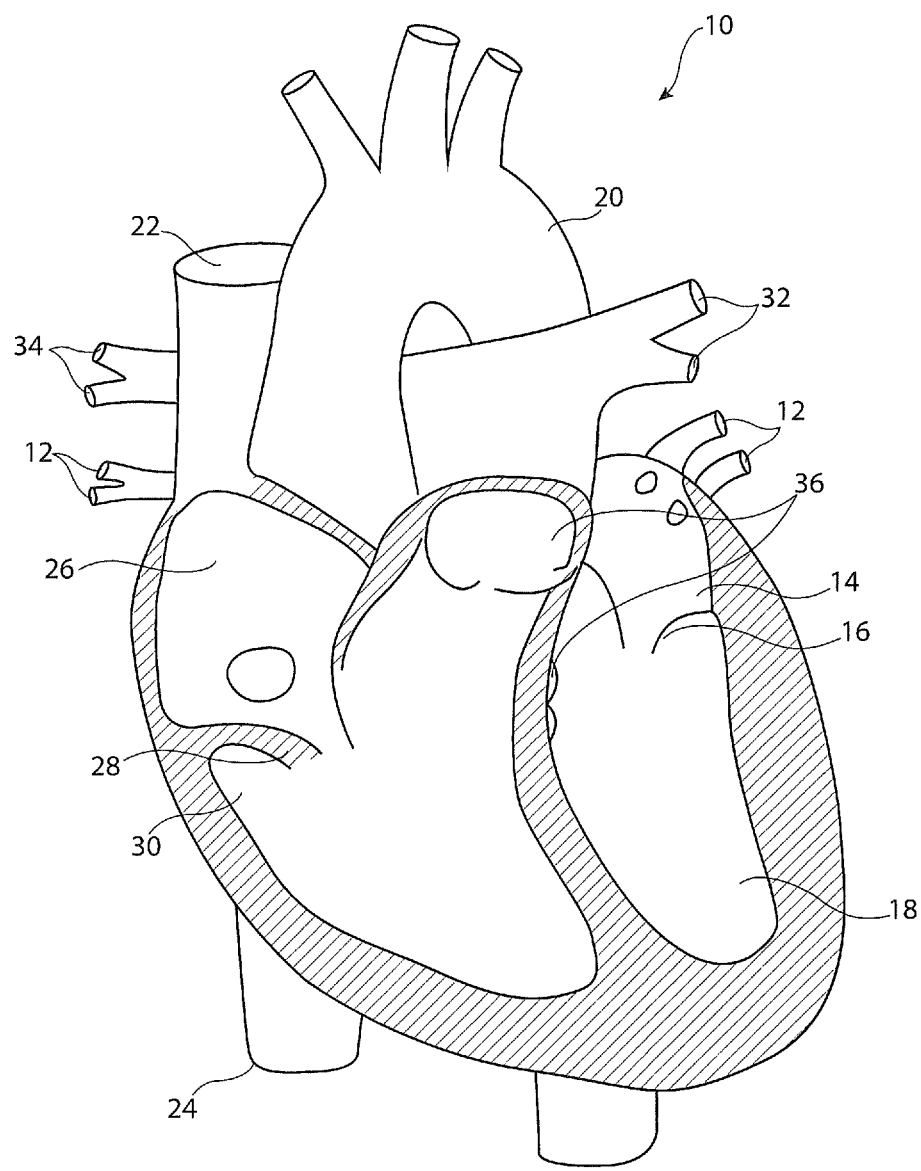
FIG. 1 shows an example of a human heart with a valvuloplasty balloon positioned across the mitral valve leading to the left ventricle.

Referring to FIG. 1, there is shown in schematic form an example of a human heart 10. The pulmonary veins 12 feed into the left atrium 14 and therefrom through the mitral valve 16 into the left ventricle 18. The left ventricle 18 feeds into the aorta 20 for passage of oxygenated blood to the body. The superior and inferior venae cava 22, 24 feed into the right atrium 26 and therefrom through the tricuspid valve 28 into the right ventricle 30. The right ventricle 30 feeds to the left and right pulmonary arteries 32, 34 respectively. The pulmonary arteries 32 and aorta have semi lunar valves 36 for controlling the direction of blood flow as the heart 10 beats.

As mentioned above, one or more of the valves 18, 28 and 36 of the heart 10 may become defective, for example as a result of stenosis, reduced valvular function and other factors. The mitral valve 16 is particularly susceptible to reduced function and stenosis.

FIG. 1 shows a valvuloplasty balloon 40 located across the mitral valve 16, having been fed endoluminally through the pulmonary veins. In this Figure, the balloon 40 is in a deflated state, ready to be deployed. In accordance with accepted valvuloplasty procedures, the balloon 40 is inflated rapidly, so as to prize open the valve leaflet of the valve 16, up to or close to the maximum opening of the valve, that is close to the diameter of the valve seat. The forced opening of the valve 16 in this manner can cure stenosis or other causes of reduced valve function.

The valvuloplasty operation is typically carried out rapidly, that is the balloon 40 is rapidly inflated and the deflated so as to be removed from the patient. The stage of inflation of the balloon 40, as well as the varying state of the heart 10 can cause the balloon 40 to jump or slip across the valve 16 as it is inflated. If the balloon 40 jumps forwards, the tip off the balloon catheter assembly risks piercing into the wall of, in this example, the left ventricle 18. This can cause damage to the heart. Should the balloon 40 slip in the other direction, there is the risk that the balloon 40 will no longer be within the valve area and thus its inflation will fail to open the valve as desired.

Figure 2B:
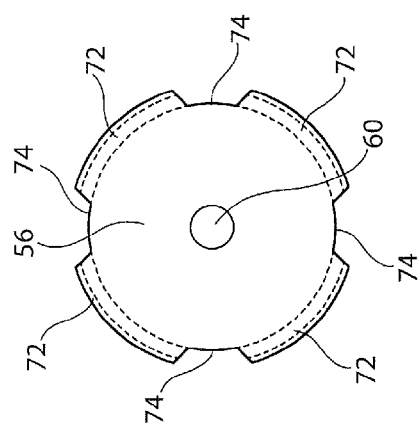
Figure 2A:
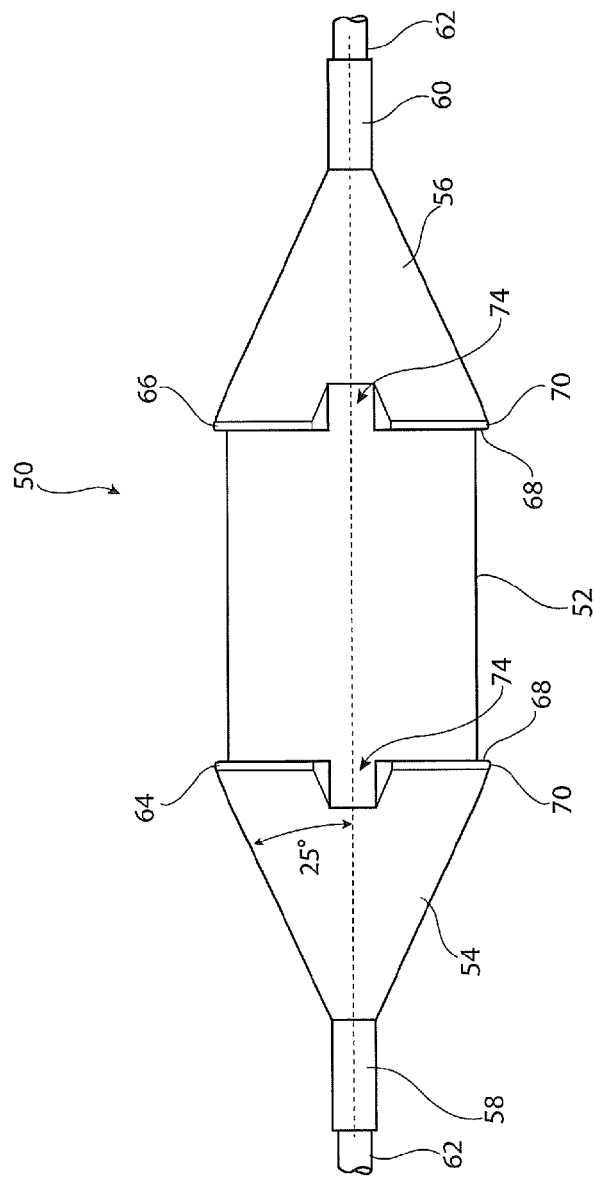
FIG. 2a is a side elevational view of an embodiment of valvuloplasty balloon.

Referring now to FIGS. 2a and 2b, there is shown an embodiment of balloon particularly suited for such valvuloplasty procedures. The balloon 50 includes a substantially cylindrical body portion 52 bounded by first and second conical portions 54, 56, each of which tapers to a respective neck portion 58, 60. The neck portions 58, 60 are sized so as to fit firmly and in a fluid tight manner to a carrier catheter 62 (as seen in FIG. 1). As is known in the art, the carrier catheter 62 includes at least one lumen with an opening within the balloon 50 to allows inflation and deflation fluid to flow into and out of the balloon 50. The carrier catheter 62 may also include other lumens, such as one for a guide wire (not shown).

The conical end portions 54, 56 are provided, in this embodiment, with raised circumferential shoulders or ribs 64, 66, which have a radial dimension or height which is greater than the radius of the body portion 52. As a result, the shoulders 64, 66 provide a retaining wall 68 which, in the preferred embodiment, is at an interior angle (that is the angle characterising the rotation of the line defining the balloon wall, through the bulk of the balloon, to the longitudinal axis) of at least 70 degrees relative to the line of the body portion, more preferably at least 80 degrees and most preferably around 90 degrees. The shoulders 68 end in a chamfered portion 70 which is preferably rounded. Thus, it is to be understood that only a portion of the shoulders 64, 66 may have these angles.

As can be seen in FIG. 2a, the conical wall of the portions 54, 56 has an interior angle of around 25 degrees in this embodiment, against an interior angle of close to 90 degrees for the retaining shoulders 68.

The shoulders 64, 66 preferably have a height of at least 0.5 millimeters and preferably of between 0.5 to 4.0 millimeters when inflated. Such a height will enable the shoulders 64, 66 to provide effective retention of the balloon 50 across a valve.

The provision of rear or opposing walls to the ribs 64, 66, in this case the conical walls of the ends 54, 56, which have a shallower angle enables the balloon 50, should it be necessary, to be pushed or pulled into the zone of a valve, with the valve sliding up the shallow angle of these walls, and into position across the cylindrical portion 52 of the balloon 50. Once in this position, the shoulders 64, 66 prevent the slippage of the balloon out of position.

The balloon 50 is made in this embodiment from a substantially consistent and unitary layer of material, including the shoulders 64, 66. It is to be understood that the layer could be formed as a sandwich of a plurality of sub layers if desired. As a result, the shoulders 64, 66 are inflatable to the shape shown in FIGS. 2a and 2b and thus collapsible when the balloon 50 is deflated.

The shoulders 64, 66 are not continuous around the entire is circumference of the balloon 50 and instead preferably segmented into a plurality of part circular segments 72, as can be seen in particular in FIG. 2b. Between adjacent segments 72 there are provided zones 74 which could be described as tethers. These zones 74 have, in this embodiment, dimensions similar to those of the body portion 52 and could be described as extensions of the body portion 52, extending to the conical ends in such a manner that the tethers 74 has the same diameter as the body portion 52. The tethers limit the amount by which the balloon 50 can inflate, particularly at the interface between the body portion 52 and the conical ends 54, 56. Thus, inflation of the balloon 50 cannot stretch the shoulders 64, 66 to an extent which would cause these to flatten. In the absence of such tethers 74, the balloon 50 would continue to expand until the shoulders 64, 66 become substantially flattened and therefore lose their features.

The number of segments 72 can be a matter of preference and choice. In the preferred embodiment, each shoulder 64, 66 is formed of four segments 74.

In other embodiments, the balloon 50 could be provided with internal tethers to maintain the integrity of the shoulders 64, 66. These embodiments are not, however, preferred.

In the embodiment shown in FIG. 2a the balloon 50 has a length of around 97 mm and an overall width of its cylindrical portion 52 of around 22 mm. The cylindrical portion 52 has a length in the region of 30 mm and is designed specifically for the treatment of a mitral valve such as the valve 16 shown in FIG. 1. The neck portions have a typical length of around 10 mm, in order to provide good sealing to the carrier catheter 62. The neck portions 58, 60 also have a diameter in the region of 4 mm, which is about the same as the diameter of the carrier catheter 62. As can be seen, in this example, the conical end portions 54, 56 taper at an interior angle of 25° to the longitudinal axis of the balloon 50. These are preferred dimensions for the specific medical application to which they are intended, that is the treatment of an adult valvular procedure. It will be apparent, however, that the dimensions of the balloon 50 will vary, both in terms of overall scale and in terms of length and diameter in dependence upon the particular medical application. As explained above, for instance, it is important that the balloon 50 should inflate to no more than the diameter of the valve seat of the particular valve to be treated. Similarly, the length of the balloon although being dependent large part upon the dimensions of the valve and also the space available for the balloon.

Figure 3B:
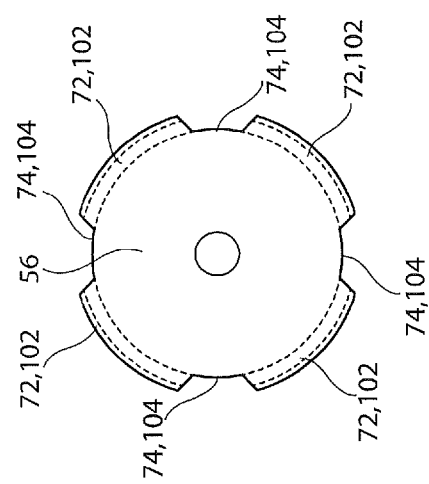
Figure 3A:
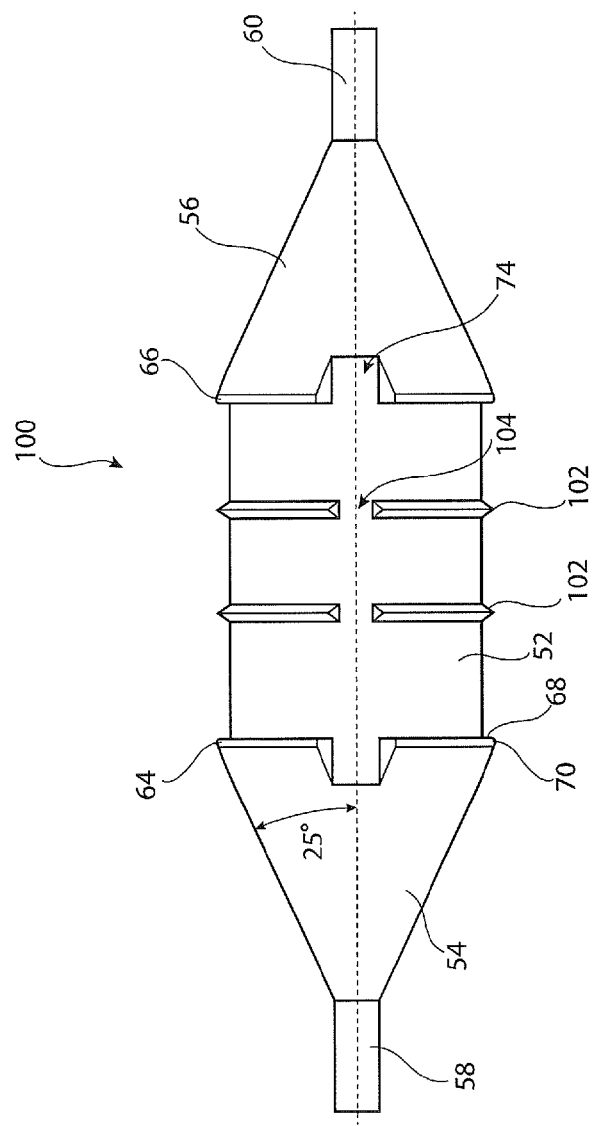
FIG. 3a is a side elevational view of another embodiment of valvuloplasty balloon.

Referring now to FIGS. 3a and 3b, there is shown another embodiment of balloon assembly 100 which has the same characteristics and features of the embodiment of FIGS. 2 and 2a and described above, with the addition of intermediate ribbing 102 located on the cylindrical portion 52 of the balloon 100. In this embodiment, there are provided two additional rib elements 102, which are equally spaced along the cylindrical portion 52 of the balloon 100. In this example, the ribs 102 leave the centre of the cylindrical portion 52 free of any intermediate ribbing. However, the number and position of intermediate ribs 102 can be different from those shown in FIG. 3a. For instance, there can be provided just a single intermediate rib 102 or more than 2 and these could be spaced non-symmetrically along the cylindrical portion 52 of the balloon 100. In this embodiment, the intermediate ribs 102 have a width of around 2 mm and a height of around 0.5 to around 1.0 mm when inflated. The intermediate ribs 102 preferably have symmetrical side walls, that is walls which are at equal but opposing interior angles to the longitudinal axis of the balloon 100, as opposed to the asymmetric arrangement of the end shoulders 64, 66. The intermediate ribs 102 provide additional securing of the balloon 100 during its use and in particular can prevent the balloon 100 from sliding when located within a valve.

As with the shoulders 64, 66, it is preferred that the intermediate ribs 102 are inflated from conventional balloon wall material, that is that they are not solid elements, although the latter is a possible alternative as is providing the intermediate ribs 102 as separate elements which are fixed to the balloon wall. In the preferred embodiment, the intermediate ribs 102 are also discontinuous and may be in four separate sections, consistent with and aligned with the section 72 following the end shoulders 64, 66. Similarly to the shoulders 64, 66, the intermediate ribs 102 are separated from one another by tethers 104, which could be described as unmodified portions of the cylindrical section 52 of the balloon 100. These tethers 104 limit the inflation of the balloon 100 and in particular of the cylindrical portion 52 to ensure that the intermediate ribs 102 do not flatten when the balloon 100 is inflated.

Even though the embodiment shown in FIGS. 3a and 3b has intermediate ribs 102 which have the same number of sections as the end shoulders 64 and 66 and tethers 104 which are aligned with one another with respect to the adjacent ribs 102 and aligned with the tethers 74 of the end sections 64, 66, this is not necessarily the case. The various sections forming the end shoulders 64, 66 and the intermediate ribs 102 can be circumferentially non-aligned and this can also apply with respect to the end shoulder 64, 66 of the embodiment of FIGS. 2a and 2b.

Figure 4:
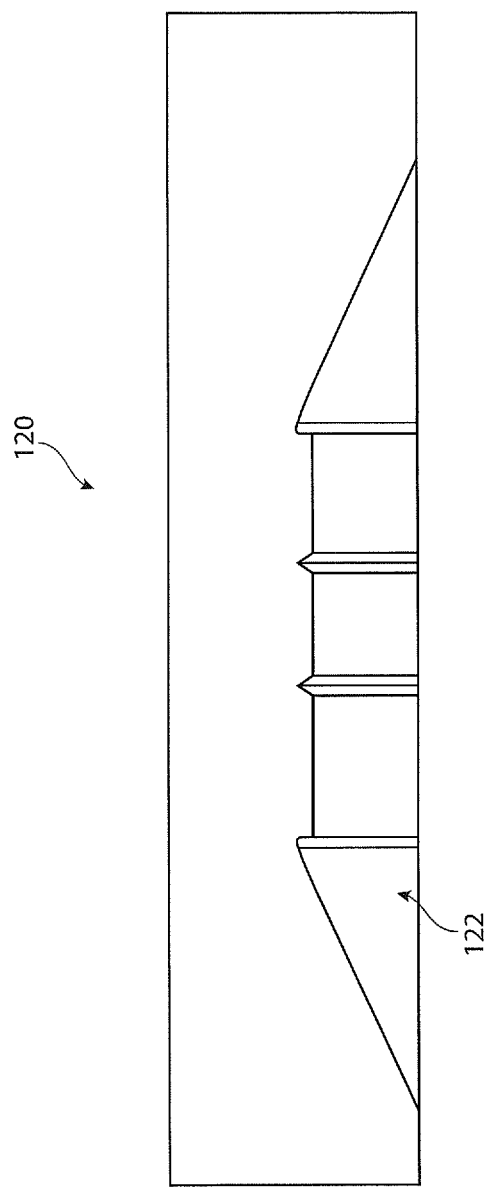
FIG. 4 is a cross-sectional view, in side elevation, of a part of an example of mold for use in the production of a balloon as shown in FIG. 3.

Referring now to FIG. 4, there is shown in schematic form a view of a part of a mold 120 for forming the balloon 100 of the embodiment of FIGS. 3a and 3b. The mold 120, which would typically be formed of a plurality of sections which are connected to one another, provides an internal surface 122 which has a contour equivalent to the contour of the balloon 100 when this is fully inflated. In other words, the contour 122 has grooves and recesses that are shaped to accommodate the various features 52-104 of the balloon 100. In this manner, when a raw tubing for the formation of the balloon 100 is inserted within the cavity of the mold 120 and inflated, the raw tubing is inflated against the wall 122 to keep or develop the shape of the various features of the balloon 100. As the balloons contemplated herein can be formed by known techniques, it is not necessary to describe in detail the method of their manufacture.

Although the shoulders or ribs 64 and 66 are, in the embodiments of FIGS. 2 and 3, shown to be integral with the conical segments 52, 54 of the balloon 50, this is not necessary. In other embodiments, the ribs 64, 66 could be located on the cylindrical portion 52 of the balloon 50, adjacent but not part of the ends 54, 56. In this embodiment, the ribs would still have the feature of providing a substantially "vertical" retention wall facing the longitudinal centre point of the balloon 50 and walls on their opposite sides which has a shallower angle.

The balloon 50 is preferably made of a substantially non-compliant material such as Pebax, nylon 12, polyethylene, PET and polyurethane. By substantially non-compliant it is meant that the balloon will inflate to a reliable and substantially consistent diameter at a given inflation pressure.

FIGS. 5 and 6 show other embodiments of balloon 100' and 100". The balloons in these embodiments are substantially the same as the embodiments described above and differ only in the shape of the body portion 153, 252. They thus have all of the features and elements of the above described embodiments and optionally also intermediate ribs.

In the embodiment of FIG. 5 the body portion 152 of the balloon has a waisted configuration, that is it narrows towards the longitudinal centre point of the balloon 100'.

The embodiment of FIG. 6 also has a body portion 252 which narrows towards the longitudinal centre of the balloon but in this case the body portion includes a central portion 254 which is substantially cylindrical.

It is considered that the embodiments of FIGS. 5 and 6 are particularly advantageous in valvular applications as they can ensure that the balloon 100', 100" sits with its middle across the valve itself.

What is claimed is:

1. A balloon catheter assembly including an inflatable balloon provided with a body portion having a radius, first and second ends and a longitudinal axis extending through the first and second ends; the balloon being formed of balloon material; and at least one circumferentially extending inflatable rib element at or proximate one of the first and second ends, wherein the inflatable rib element is not a solid element and has a wall thickness substantially the same as that of the balloon, the inflatable rib element being formed of balloon material and being inflatable with the balloon; the inflatable rib element, when inflated, including a retaining shoulder facing the body portion of the balloon and a wall portion facing a direction opposite the body portion; wherein said retaining shoulder has an interior angle to the longitudinal axis which is greater than the interior angle of the wall portion to the longitudinal axis of the balloon; the inflatable rib element being discontinuous around the circumference of the balloon and being formed of a plurality of circumferentially aligned inflatable rib portions spaced circumferentially from one another by a tether element; the tether element extending to the retaining shoulder and having a radial dimension or height not less than the radius of the body portion; and the inflatable rib element having a radial dimension or height which is greater than the radius of the body portion when the balloon is fully inflated to a maximum diameter; and the inflatable rib element having a radial dimension or height which is greater than the radius of the body portion when the balloon is fully inflated to a maximum diameter.

2. An assembly according to claim 1, wherein the inflatable rib has a wedge shape.

3. An assembly according to claim 1, wherein the retaining shoulder has an interior angle to the surface of the body member which is at least 70 degrees.

4. An assembly according to claim 1, wherein the retaining shoulder has an interior angle to the surface of the body member which is at least 80 degrees.

5. An assembly according to claim 1, wherein the retaining shoulder has an interior angle to the surface of the body member which is substantially 90 degrees.

6. An assembly according to claim 1, wherein there are provided first and second inflatable ribs, located at or proximate the first and second ends of the body portion of the balloon, each of said first and second inflatable ribs having a retaining shoulder facing the opposing end of the balloon and a wall portion at or facing the end of the balloon at which the inflatable rib is located.

7. An assembly according to claim 1, wherein the or each inflatable rib has an inflated height of at least 0.5 millimeters.

8. An assembly according to claim 1, wherein the or each inflatable rib has an inflated height of between 0.5 mm and 4.0 mm.

9. An assembly according to claim 1, wherein the inflatable rib or ribs are formed of the same material as the body portion of the balloon.

10. An assembly according to claim 1, wherein the inflatable rib or ribs are a continuation of the balloon wall.

11. An assembly according to claim 1, wherein the or each tether element is an extension of the cylindrical body portion of the balloon.

12. An assembly according to claim 1, including at least one intermediate inflatable rib extending circumferentially around the body portion.

13. An assembly according to claim 12, including two or more such intermediate inflatable ribs, spaced from one another.

14. An assembly according to claim 13, wherein the intermediate inflatable ribs are spaced evenly along the body portion of the balloon.

15. An assembly according to claim 12, wherein the or each intermediate inflatable rib has an inflated height which is less than the inflated height of the end inflatable rib or ribs.

16. An assembly according to claim 12, wherein the or each intermediate inflatable rib has an inflated height of at least 0.5 millimeters.

17. An assembly according to claim 1, wherein the body portion has an inflated diameter of around 18 mm to 25 mm.

18. An assembly according to claim 1, wherein the balloon is made from a substantially non-compliant material.

19. A balloon catheter assembly comprising;
an inflatable balloon further comprising;
a body portion having a radius, first and second ends and a longitudinal axis extending through the first end and second ends; and
at least one circumferentially extending inflatable rib element at or proximate one of the first and second ends, wherein the inflatable rib element is not a solid element and has a wall thickness substantially the same as that of the balloon, the inflatable rib element, when inflated, including a retaining shoulder facing the body portion of the balloon and a wall portion facing a direction opposite the body portion; the inflatable rib element being discontinuous around the circumference of the balloon and being formed of a plurality of circumferentially aligned inflatable rib portions spaced circumferentially from one another by a tether element; the tether element extending to the retaining shoulder and having a radial dimension or height not less than the radius of the body portion; and the inflatable rib element having a radial dimension or height which is greater than the radius of the body portion when the balloon is fully inflated to a maximum diameter; and the inflatable rib element having a radial dimension or height which is greater than the radius of the body portion when the balloon is fully inflated to a maximum diameter.

20. A balloon catheter assembly including an inflatable balloon provided with a body portion having a radius, first and second ends and a longitudinal axis extending through a first end and a second end; and at least one circumferentially extending inflatable rib element at or proximate one of the first and second ends, wherein the inflatable rib element is not a solid element and has a wall thickness substantially the same as that of the balloon, the inflatable rib element being inflatable and collapsible with the balloon; the inflatable rib element, when inflated, including a retaining shoulder facing the body portion of the balloon and a wall portion facing a direction opposite the body portion; wherein said retaining shoulder has an interior angle to the longitudinal axis which is greater than the interior angle of the wall portion to the longitudinal axis of the balloon; the inflatable rib element being discontinuous around the circumference of the balloon and being formed of a plurality of circumferentially aligned inflatable rib portions spaced circumferentially from one another by a tether element; the tether element extending to the retaining shoulder and having a radial dimension or height not less than the radius of the body portion; and the inflatable rib element having a radial dimension or height which is greater than the radius of the body portion when the balloon is fully inflated to a maximum diameter; and the inflatable rib element having a radial dimension or height which is greater than the radius of the body portion when the balloon is fully inflated to a maximum diameter.

\* \* \* \* \*